United States Patent [19]

Bishop

[11] Patent Number: 5,408,576
[45] Date of Patent: Apr. 18, 1995

[54] IV FLUID WARMER

[76] Inventor: Robert A. Bishop, 13726 Creekside, Dallas, Tex. 75240

[21] Appl. No.: 967,434

[22] Filed: Oct. 28, 1992

[51] Int. Cl.$^6$ .............................................. H05B 1/00
[52] U.S. Cl. .................................... 392/470; 219/521; 219/386
[58] Field of Search ...................... 392/470, 443, 444; 219/385, 386, 387, 521, 528

[56] References Cited

U.S. PATENT DOCUMENTS

| | | | |
|---|---|---|---|
| 1,659,719 | 2/1928 | Blake | 219/385 |
| 2,214,215 | 9/1940 | Watermann | 392/444 |
| 2,576,874 | 11/1951 | Acton | 219/385 |
| 2,713,112 | 7/1955 | Mills | 219/521 |
| 4,233,495 | 11/1980 | Scoville | 219/386 |
| 4,523,078 | 6/1985 | Lehmann | 219/386 |
| 4,707,587 | 11/1987 | Greenblatt | 392/470 |
| 4,889,973 | 12/1989 | Farinacci | 219/528 |
| 5,183,994 | 2/1993 | Bowles | 219/521 |

Primary Examiner—Teresa J. Walberg
Attorney, Agent, or Firm—Aquilino & Welsh

[57] ABSTRACT

A cabinet structure is specially adapted for receiving a plurality of IV fluid bags. When IV bags are placed inside this cabinet structure, the user turns on a power switch to begin a very specific and controlled heating cycle. A temperature indicator on the front of the cabinet allows the user to ascertain when the desired temperature has been reached. When an IV bag is desired for use, it is removed directly from the side of the cabinet through an opening approximately the size of the IV bag. A temperature sensor inside the bag compartment allows for automatic regulation of the temperature of a pad of heating filaments located along the back face of the inside the cabinet. The heating elements are covered by a rubber layer to protect the bags from melting. The cabinet structure can be fastened to any IV pole, hung on the side of an anesthesia cart or be mounted directly to a wall.

16 Claims, 3 Drawing Sheets

IV FLUID WARMER

BACKGROUND OF THE INVENTION

1. Field of the Invention

The present invention relates to warming fluids, and in particular, to warming IV fluid solution bags for use in the medical field. The present invention uses a safe and unique apparatus to heat and store a plurality of IV bags at the locations where they are to be used.

2. Description of the Prior Art

The availability of a reliable and convenient source of warm (105° F./40° C.) intravenous fluid solution is important in medical applications and more particularly in an operating environment where large quantities of IV fluids may be necessary.

Systems found in the prior art often require depletion of the self-contained sterilized IV fluid bag/container to heat the fluid. Removal of the fluid introduces unnecessary risk (i.e., contamination) and fails to provide for a regulated supply which is simple to use and is a convenient source of warmed IV fluid solutions. These prior art systems often require large and complex devices requiring a circulation unit to withdraw the fluid from a bag or other storage container. The removed fluids are then distributed across or through a variety of heating sources and returned to a separate container. Examples of such prior art systems may be found in the following U.S. Pat. Nos. to Rosner (4,678,460), Ogawa (4,293,762), Le Boeuf (4,309,592), Kurucz (4,844,074), van Leerdam (4,906,816) and Jewett (4,464,563). Each of the above cited patents show systems where removing the fluid is essential for proper heating.

Prior art references directed to heating a fluid without removal of the fluid are detailed below. Each of the references fail to provide for a configuration similar to that of the present invention.

The U.S. Pat. No. to White (4,936,336) is an apparatus and method for the warming of intravenous equipment consisting of an insulated wrap material having a removable and reusable heat pack. This reference fails to provide for a regulated source of heat integrated within a cabinet structure. To provide for a reliable heating source requires strict attention to temperature changes and distribution thereof. The heating source of White is a heat pack which does not maintain a specified thermal transfer ratio throughout the heating cycle and must be reheated and replaced each time heating is to take place. White is also limited to, at the most, two intravenous bags and has no provisions for adding additional bags. This becomes a problem in the operating room environment where a large quantity of heated bags are needed.

The U.S. Pat. Nos. to Nicholas Marchiani Chatelain et al. (4,874,033) and Auerbach (4,801,777) are directed to methods and apparatuses for heating blood products. Both of these references require the submerging of a blood bag in water which is then heated by some means. Applicant's invention is not directed to heating blood products and further requires no source of water to operate. The requirement of providing a water source limits these devices to locations to where an immediate source of water is available. Applicant's instant invention can be used anywhere. The invention also is more convenient as no fluids other than the fluid to be heated are introduced into the system.

The U.S. Pat. No. to Coffey (4,657,004) is a mobile livestock intensive care unit having a temperature controlled fluid/medicine chamber. This reference fails to provide for applicant's specific heating cabinet structure and associated electronics.

SUMMARY OF THE INVENTION

A general object of the present invention is to provide for a safe source of warmed IV fluid.

Another object of the present invention is to provide for said source of warmed IV fluid to be readily available wherever and whenever it is needed.

Another object of the present invention is to provide for a convenient and relatively simple method and apparatus to heat IV fluid solutions.

Another object of the invention is to provide for a method of heating IV fluids within the container they are most commonly found, a bag, without removal of the fluid therefrom.

Another object of the present invention is to provide for a regulated source of heat to ensure nondestruction of the IV fluid solution.

Another object of the present invention is to provide for versatile attachment of the heating apparatus depending on the use and location needed.

In accordance with these and other objects of this invention, this invention provides for a self-contained IV fluid warmer. The invention has a cabinet structure specially adapted for receiving a plurality of IV fluid bags. When IV bags are placed inside this cabinet structure, the user turns on a power switch to begin a very specific and controlled heating cycle. A temperature indicator on the front of the cabinet allows the user to ascertain when the desired temperature has been reached. When an IV bag is desired for use it is removed directly from the side of the cabinet through an opening approximately the size of the IV bag. Because of the structure of the cabinet, the bag which has remained in the cabinet the longest is automatically the first to be removed, with the newest bags being added to the cabinet from a top access opening. A temperature sensor inside the bag compartment allows for automatic regulation of the temperature of a matrix of heating filaments located along the back face of the inside of the cabinet. The heating elements are covered by a rubber layer to protect the bags from melting when in contact therewith. The cabinet structure can be fastened to any IV pole, hung on the side of an anesthesia cart or be mounted directly to a wall.

Other objects and advantages of the present invention will become apparent from the following detailed description when viewed in conjunction with the accompanying drawings, which set forth certain embodiments of the invention.

BRIEF DESCRIPTION OF THE DRAWINGS

A detailed description of a preferred embodiment of this invention is made in conjunction with the following drawings in which like reference numerals are used in the different figures for illustrating the same elements.

DESCRIPTION OF THE PREFERRED EMBODIMENTS

The detailed embodiments of the present invention are disclosed herein, however, it is to be understood that the disclosed embodiments are merely exemplary of the invention, which may be embodied in various forms. Therefore, the details disclosed herein are not to be interpreted as limited, but merely as the basis for the claims and as a basis for teaching one skilled in the art how to make and/or use the invention.

Figure 1:
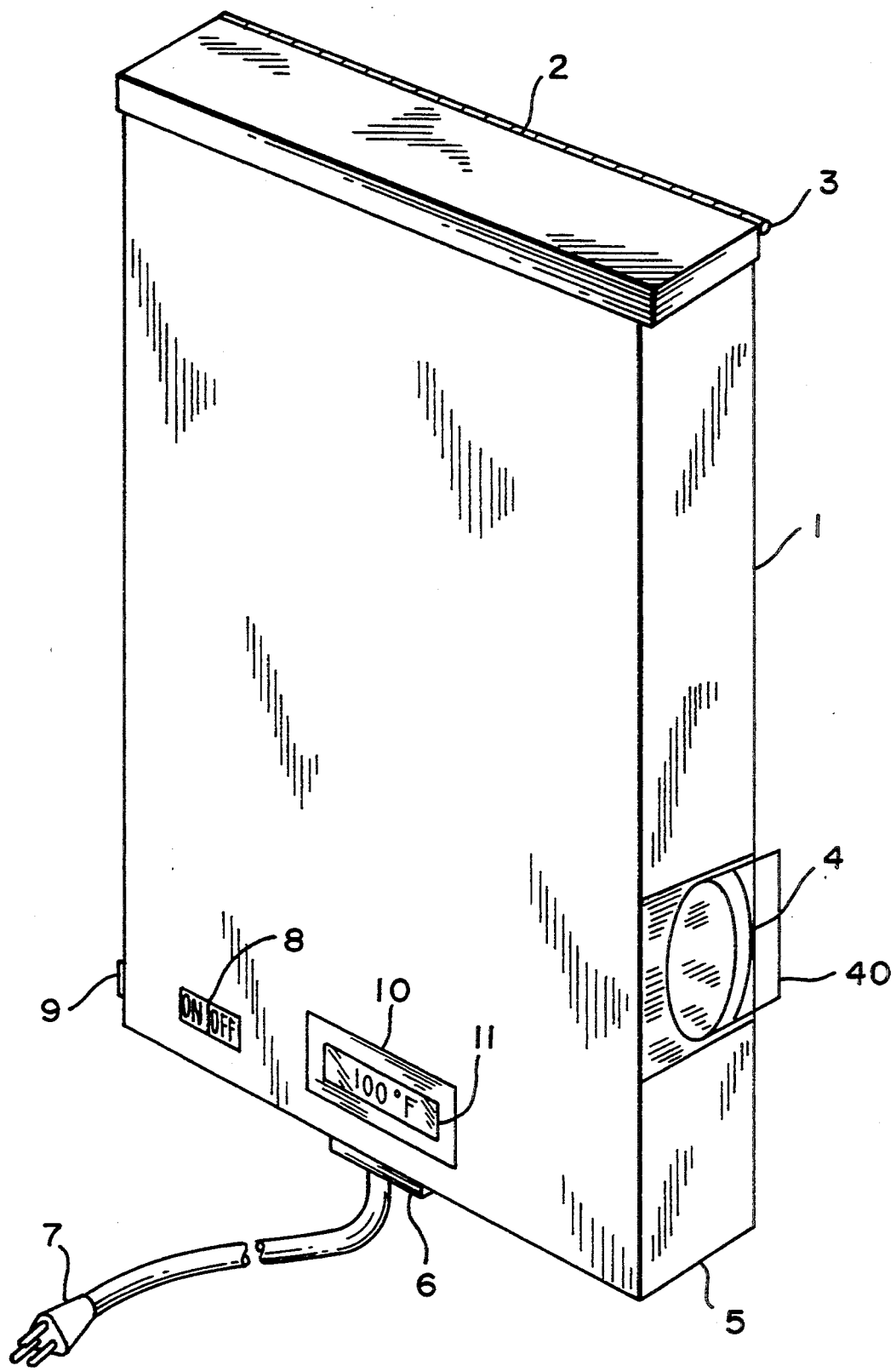
FIG. 1 is an external perspective view of the IV fluid warming cabinet structure of the present invention.

Referring to the drawings and, in particular, to FIG. 1, there is shown a cabinet structure in accordance with the teachings of the present invention. The cabinet structure 1 is rectangular in shape with a width and depth of approximately the respective length and thickness of an IV fluid bag (40) and a height designed to be of a size to accommodate a plurality of longitudinally stacked IV fluid bags. Having a width of approximately the thickness of an IV bag allows for a maximum surface area to be in continuous contact with a heating pad 16 (described in detail hereafter). In the preferred embodiment, the height is designed to enable the cabinet 1 to hold five IV fluid bags. The cabinet 1 has a cover 2 which is pivotable along the length of hinge 3. The cover which opens upwardly from the front is used to load IV bags into the cabinet 1. On the right side of the cabinet 1 is an opening 4 which is approximately the size of a cross section of the longitudinally loaded IV fluid bag. The opening 4 is used for removing a heated IV fluid bag. The lowest edge of the opening 4 represents the lowest vertical point that the IV bags descend into the cabinet. Element 5 is a base plate for the bottom of the cabinet 1.

Located on the front of the cabinet 1 is a conventional digital temperature indicator 11 used to indicate the temperature inside the cabinet 1. A plastic bracket structure 10 is used for attaching the temperature indicator 11 to the cabinet 1 and further for encapsulating its associated electronics (not shown). An on/off switch 8 is conveniently located on the front of the cabinet 1 and is used to connect power to the cabinet to start the heating cycle.

Located on the left side of the cabinet 1 is a 15 amp fuse (not shown) which has an associated reset button 9 to protect the device from overcurrent/overvoltage problems which could damage the device. Located on the bottom of the cabinet 1 is a threaded collar 6 through which extends a three prong power cord 7.

Figure 2:
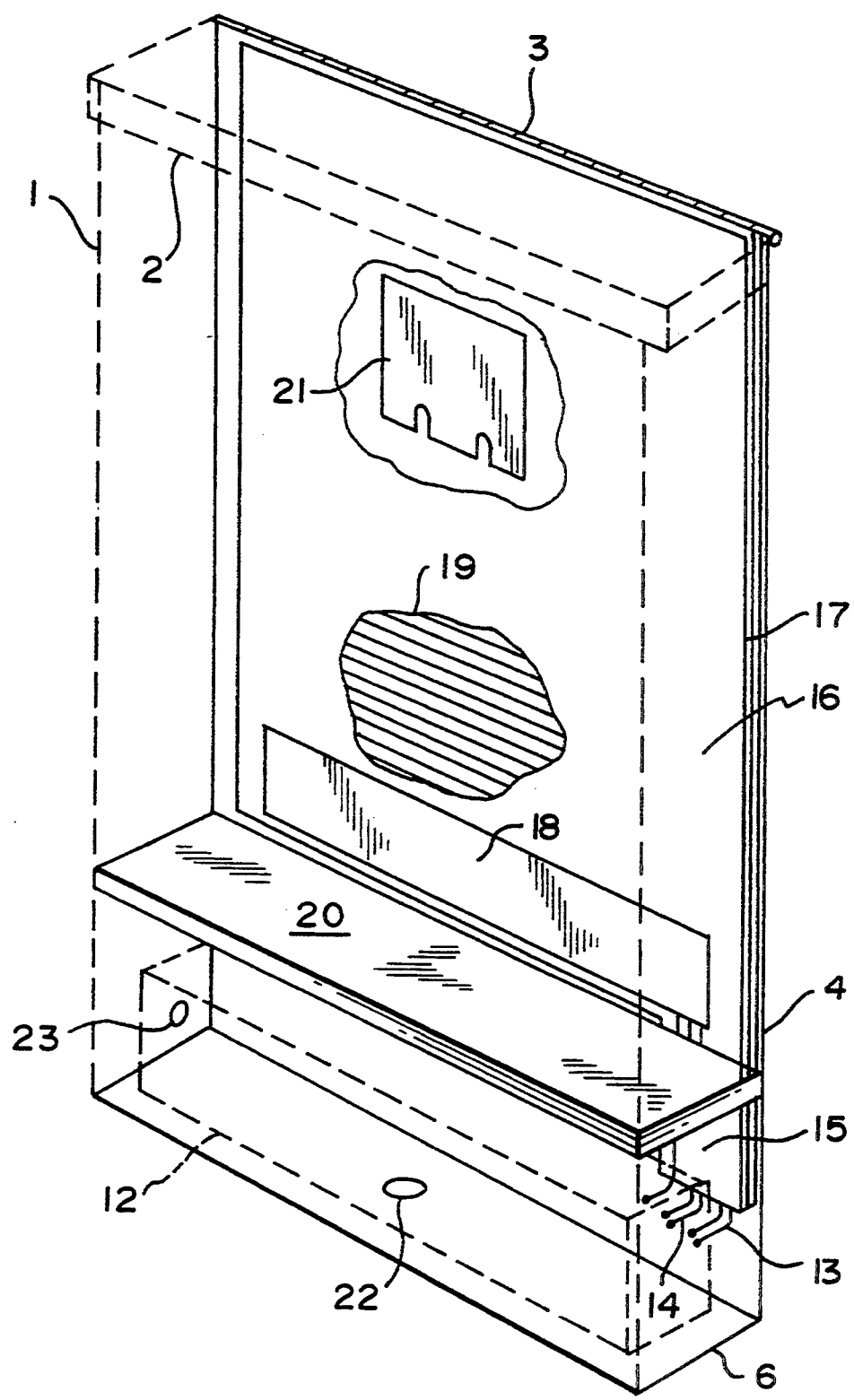
FIG. 2 is an internal perspective view of the IV fluid warming cabinet of FIG. 1.

FIG. 2 shows a cutaway perspective of the cabinet structure 1 as shown in FIG. 1. Located between the lowest vertical point of the opening 4 and the base plate 5 is a compartment for holding the associated electronics 12 (shown in block form and in detail in FIG. 3) of the IV fluid warming device. Extending upwardly from the electronics 12 are a pair of red wires 13 which are connected to, and provide power, to the heating pad 16. The heating pad 16 covers substantially the entire area of the back side of the cabinet 1 with a small section extending downwardly below the opening 4 to allow for connection to the electronics 12. The heating pad consists of a thin sheet of longitudinally spaced filaments 19 (shown as a cutout). On top of these filaments 19 is a thin sheet of silicon rubber 17 to prevent burning or melting of the IV fluid bags as they come in contact with the heading pad 16 during the heating cycle. The heating pad sheet 16 including the rubber layer 17 is secured to the back of the cabinet 1 by a plurality of layers of a pressure sensitive adhesive. The technical specifications of the pad are: dielectric strength—1000 volts RMS at 60 Hz for 1 minute, element to outer surfaces; 5 mA maximum leakage current, temperature limit 150° C., heater resistance—60.00 ohms, 240 watts ref. at 120 volts and a noninductive filament pattern.

Located at the bottom of the heating pad sheet 16 is a sensor 18 also covered by an identical type layer of silicon rubber (not shown). This sensor senses the temperature of the heating pad 16 at the bottom of the cabinet 1. This is important, as this would be the location of the IV fluid bag which is loaded into the cabinet 1 first and consequentially would have been in the cabinet 1 the longest. The sensor 18 is connected to the associated electronics 12 through blue wires 14. The wires 13 and 14, are in the preferred embodiment, #24, stranded, teflon insulated per UL1180. In addition, a single wire 15 extends from the sensor 18 to the digital temperature indicator 11 to give a visual indication to the user of the device.

A foam pad 20 lies across the width of the cabinet 1 to cushion the fall of the IV fluid bags as the descend into the cabinet. The pad is secured to a metal plate (not shown) which separates the IV fluid bags from the electrical circuitry 12 and is located even with the lowest vertical point of opening 4.

Located on the back of the cabinet 1 (shown by cutout) is a back plate holder 21 for securing the cabinet 1 to a desired location. A suitable bracket structure, as is known in the art, can be used to secure the cabinet 1 to an IV pole or other device as desired.

A hole 22 is located in the bottom of the cabinet 1 to allow for the power cord 7 to extend through the cabinet 1. An additional hole is located on the left side to allow for the fuse reset switch 9 to extend through the cabinet.

Figure 3:
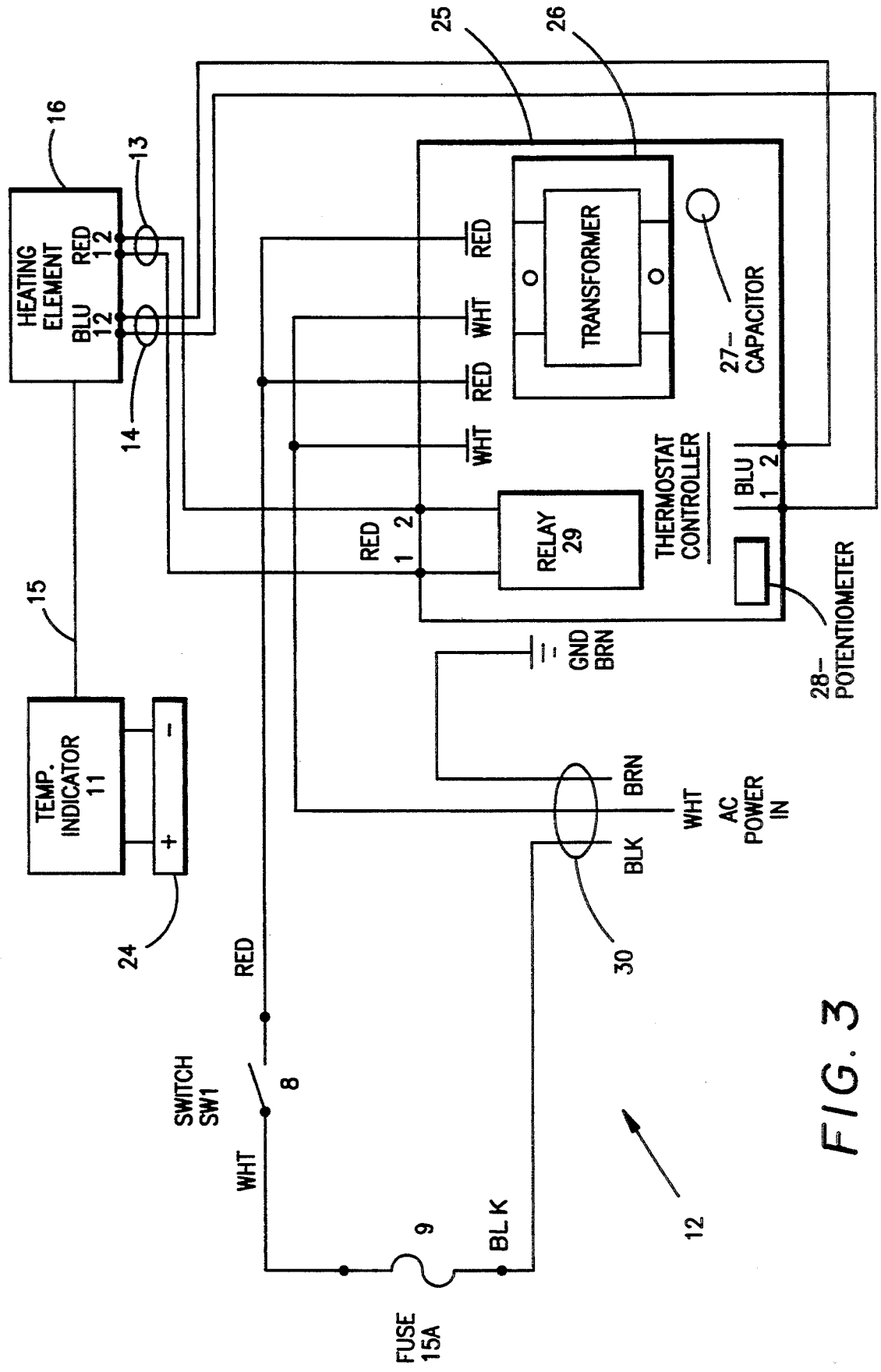
FIG. 3 is a diagram of the heater, thermostat controller, temperature sensor, and power electronics of the present invention.

FIG. 3 shows the diagrammatic details of the electronics of element 12 of FIG. 2. Thermostat controller 25 is a conventional temperature controller consisting of at least a transformer 26, capacitor 27, potentiometer 28 and relay 29 which works in a known manner to one skilled in the art. The thermostat controller 25 is preset to a temperature range appropriate for the controlled heating of IV fluid bags. In the preferred embodiment, this range would be 102°–105° F. (38°–40° C.). This thermostat controller 25 is connected to the heating pad 16 and sensor 18 through lines 13 and 14, as previously discussed. The controller is further connected to power through switch 8, fuse 9 and power cord 7 through wires 30. The power source for the digital temperature indicator 11 is a battery 24. The digital temperature indicator is connected through wire 15 to the sensor 18.

The operation of the IV fluid warmer goes as follows. The cabinet structure is first secured to a desired location using back plate holder 21 or a clamping bracket if it is to be secured to an IV pole. The unit must then be connected to an electrical source through power cord 7. The unit is loaded by opening of the top cover 3 and placing one or more IV fluid bags longitudinally into the cabinet. The bags will stack up on top of each other with the bottom bag resting on the foam pad 20. The user then turns on switch 8 to start the heating cycle. The thermostat controller 25 will energize the heating pad 16 for approximately 45 minutes. As the heating cycle proceeds, the sensor 18 relays the temperature across the bottom section to both the thermostat controller 25 and digital temperature indicator 11. The thermostat controller keeps the heating pad 16 in a specific temperature range as previously discussed while the digital temperature indicator 11 provides the user with a visual indication of the temperature of the heating pad 16. The user may remove IV fluid bags from the side through opening 4 as desired. The unit may be left on or turned off and on as desired.

The IV fluid warmer or the present invention overcomes many of the problems associated with prior art fluid warmers. The IV fluid warmer brings to each and every operating room, anesthesiologist, surgeon and most importantly the patient, a readily available supply of warm (105° F./40° C.) IV fluids. Any and all IV solutions may be placed into the unit without fear of being ruined, rendered unusable or delivered to the patient at improper or dangerous temperatures. The unit may be fastened to any IV pole, hung on the side of an anesthesia cart or mounted on the wall. Five IV solution bags may be stored and warmed simultaneously with optimum solution delivery temperature reached in approximately 45 minutes. The unit may be turned on or off as desired and can be easily loaded and unloaded.

While the foregoing description represents the preferred embodiment, it should be recognized that the invention could be practiced in various configurations and with equivalent functional elements without departing from the scope of the invention.

I claim:

1. A fluid warming apparatus comprising:
   a cabinet structure adapted to receive a plurality of fluid containers, said cabinet structure having an access opening in one wall thereof for individual removal of the plurality of fluid containers, said access opening being permanently open;
   a thin multilayered heating pad covering one side of an internal wall of said cabinet structure;
   a sensor located within a portion of said heating pad for sensing the temperature of said pad;
   a thermostat controller contained within said cabinet structure and connected to said heating pad for regulating the temperature of said pad;
   a digital temperature indicator located externally on said cabinet structure and connected to said heating pad to provide a visual temperature indication; and,
   an on/off switch for providing power to said thermostat controller to start a preset heating cycle to warm said plurality of fluid containers.

2. A fluid warming apparatus as per claim 1, wherein said fluid containers are IV fluid containers.

3. A fluid warming apparatus as per claim 1, wherein said thin multilayered heating pad comprises a rubber outer layer, an internal metallic array of heating elements and a multilayered pressure sensitive adhesive backing.

4. A fluid warming apparatus as per claim 3, wherein said sensor is located beneath said rubber outer layer.

5. A fluid warming apparatus as per claim 1, wherein said thermostatic controller is located in a separate compartment in said cabinet structure, separating it from the heating pad assembly.

6. A fluid warming apparatus as per claim 5, wherein said thermostatic controller is preset to a temperature range of 102°-105° F. (38°-40° C.).

7. A fluid warming apparatus as per claim 1, wherein said cabinet structure is adapted to receive up to 5 fluid containers.

8. A fluid warming apparatus as per claim 1 wherein said sensor is located adjacent said opening in said side wall.

9. A fluid warming apparatus as per claim 1 wherein said cabinet structure includes a securing means for mounting the apparatus in an upright position.

10. A fluid warming apparatus comprising:
    a cabinet structure including front, back, top, bottom and side walls forming an enclosure with an opening in one of said side walls for removal of fluid containers one at a time, said top wall being openable to allow for insertion of a plurality of containers;
    a thin multilayered heating pad covering one side of an internal wall of said cabinet structure;
    a sensor located within a portion of said heating pad adjacent said opening in said side wall for sensing the temperature of said pad;
    a thermostat controller connected to said heating pad for regulating the temperature of said pad; and,
    an on/off switch for providing power to said thermostat controller to start a preset heating cycle to warm said plurality of fluid container.

11. A fluid warming apparatus as per claim 10, wherein said thin multilayered heating pad comprises a rubber outer layer and internal metallic array of heating elements and a multilayered pressure sensitive adhesive backing.

12. A fluid warming apparatus as per claim 10, wherein said sensor is located beneath said rubber outer layer.

13. A fluid warming apparatus as per claim 10, wherein said thermostatic controller is located in a separate compartment in said cabinet structure, separating it from the heating pad assembly.

14. A fluid warming apparatus as per claim 9, wherein said cabinet structure is adapted to receive up to 5 fluid containers.

15. A fluid warming apparatus as per claim 10 wherein said cabinet structure includes a securing means for mounting the apparatus in an upright position.

16. A fluid warming apparatus as per claim 10, wherein said thermostatic controller is preset to a temperature range of 102°-105° F. (38°-40° C.).

* * * * *